United States Patent [19]

Sibalis et al.

[11] Patent Number: 4,940,456
[45] Date of Patent: Jul. 10, 1990

[54] ELECTROLYTIC TRANSDERMAL DELIVERY OF PROTEINS

[76] Inventors: Dan Sibalis, 268 Hallock Rd., Stony Brook, N.Y. 11790; Sanford Rosen, 64 E. 86th St., New York, N.Y. 10028

[21] Appl. No.: 279,315

[22] Filed: Dec. 1, 1988

Related U.S. Application Data

[63] Continuation of Ser. No. 12,898, Feb. 10, 1987, abandoned.

[51] Int. Cl.$^5$ .............................................. A61M 37/00
[52] U.S. Cl. ....................................... 604/20; 128/798; 424/449
[58] Field of Search ................... 604/20; 128/798, 802, 128/803; 424/447, 448, 449

[56] References Cited

U.S. PATENT DOCUMENTS

| | | | |
|---|---|---|---|
| 4,183,849 | 1/1980 | Hansen et al. | 530/305 |
| 4,234,570 | 11/1980 | Kanbayashi et al. | 530/395 |
| 4,391,904 | 7/1983 | Litman et al. | 435/805 |
| 4,403,984 | 9/1983 | Ash et al. | 128/632 |
| 4,459,226 | 7/1984 | Grimes et al. | 260/112.7 |
| 4,557,723 | 12/1985 | Sibalis | 604/20 |
| 4,573,996 | 3/1986 | Kwiatek et al. | 424/448 |
| 4,640,689 | 2/1987 | Sibalis | 604/20 |
| 4,666,441 | 5/1987 | Andriola et al. | 424/449 |
| 4,710,497 | 12/1987 | Heller et al. | 514/221 |
| 4,734,362 | 3/1988 | Hung et al. | 435/68 |
| 4,746,647 | 5/1988 | Svenson | 530/350 |
| 4,878,892 | 11/1989 | Sibalis | 604/20 |

OTHER PUBLICATIONS

*The Washington Post*, "Drug Treatment Through Patches Nears", 11/23/87, p. A11.
Siddiqui et al, "Facilitated Transdermal Transport of Insulin", *Journal of Pharmaceutical Sciences*, vol. 76, No. 4, 4/1987 pp. 314–315.
Kari, "Control of Blood Glucose Levels in Alloxan–Diabetic Rabbits by Iontophoresis of Insulin," *Diabetes*, vol. 35, Feb. 1986 pp. 217–221.
Stephen et al, "Potential Novel Methods of Insulin Administration: I. Iontophoresis," *Biomed. Biochim. Acta* 43 (1984) 5, 553–558.
Sato et al, "Prevention of Insulin Self–Association and Surface Adsorption," *Journal of Pharmaceutical Sciences*, vol. 72, No. 3 Mar. 1983, pp. 228–232.

*Primary Examiner*—Stephen C. Pellegrino
*Assistant Examiner*—Ralph Lewis
*Attorney, Agent, or Firm*—Lackenbach Siegel Marzullo & Aronson

[57] ABSTRACT

A chemical composition for electrolytic transdermal transport of a protein to the blood stream of the patient comprises:

(a) a protein,
(b) a cosolvent with negative Setschenow constants, and
(c) water.

Some of the preferred proteins are: insulin, protamine sulfate, calcitonin, glucagon, and corticotropin. Some of the preferred dissociating agents with negative Setschenow constants are: urea, propylurea, potassium iodide, sodium perchlorate, and guanidine hydrochloride.

The electrolytic device containing the composition to be transdermally delivered comprises:
two electrode elements separated by barrier means,
a reservoir containing the composition of the invention,
an electronic/electrolytic circuit including a source of a power,
a cover, and
adhesive means holding the device to the patient's skin.

A semipermeable membrane between the patient's skin and the electrolytic device is optional.

8 Claims, 3 Drawing Sheets

ELECTROLYTIC TRANSDERMAL DELIVERY OF PROTEINS

This application is a continuation of application Ser. No. 012,898, filed Feb. 10, 1987, now abandoned.

RELATED U.S. PATENTS AND APPLICATIONS

This application is related to U.S. Pat. Nos. 4,557,723, 4,622,031 and 4,640,689 and to copending applications Ser. No. PCT/US85/00080 filed Jan. 17, 1985; Ser. No. 702,486 filed Feb. 19, 1985; PCT/US85/01074 and PCT/US85/01075 both filed June 10, 1985; Ser. No. 778,183 filed Sept. 16, 1985; Ser. No. 807,234 filed Dec. 10, 1985; Ser. No. 839,523 filed Mar. 14, 1986.; Ser. No. 888,151 filed July 18, 1986; Ser. No. 922,296 filed Oct. 23, 1986; and Ser. No. 554 and Ser. No. 555 filed Jan. 5, 1987.

FIELD OF THE INVENTION

This invention relates to electrolytic transdermal delivery of proteins and more specifically to delivery to the blood stream of the patient of aqueous solutions or suspensions of insulin in the presence of an agent with negative Setschenow constants.

BACKGROUND OF THE INVENTION

Patents and patent applications cited above disclose basic aspects of transdermal delivery of drugs by electrical power patches on the patient's skin. Other U.S. and foreign patents also disclose transdermal electrical, and medical effects, as follows:

| U.S. Pat. No. | | |
|---|---|---|
| 385,556 | 2,267,162 | 3,163,166 |
| 486,902 | 2,493,155 | 3,289,671 |
| 588,479 | 2,784,715 | 3,547,107 |
| 3,677,268 | 4,239,052 | 4,367,745 |
| 4,008,721 | 4,243,052 | 4,367,745 |
| 4,141,358 | 4,273,135 | 4,406,658 |
| 4,164,226 | 4,290,878 | 4,419,019 |
| 4,166,457 | 4,325,367 | 4,474,570 |
| 4,239,046 | 4,362,645 | |
| Foreign Patents | | |
| EPA 58,920 | DE 2,902,021.83 | UK 2,104,388 |
| EPA 60,452 | DE 3,225,748 | |

None of these references, however, show the effective administration of protein drugs; especially high molecular weight proteins such as insulin, renin, corticortropin, calcitonin, and glucogon with structures having more than about 20 polypeptide units and molecular weights up to 40,000 daltons.

A paper entitled "Prevention of Insulin Self-Association and Surface Adsorption" by Sato, Ebert, and Kim in the Journal of Pharmaceutical Sciences 72, No. 3, 228-232, Mar. 1983 discusses the association of insulin in water to dimers, tetramers, hexamers, and higher aggregates and consequent adsorption of these polymers onto plastic surfaces such as polyurethane, silicone, rubber, and cellulose under high shear and in the presence of additives such as lysine, ethylenediaminetetraacetic acid salts, and urea.

The ionophoresis of conventional commercial insulin is termed "meaningless" with "no significant differences in changing blood glucose levels" in a paper by Stephen, Peterlenz, and Jacobsen in Biomedical Biochemical Acta 5, 553-558 (1984) experimenting on eight human volunteers. One pig was treated with an unspecified, modified, highly ionized, predominately monomeric, derivative of insulin for 20 minutes followed by a drop in blood sugar. This publication states that "a new ionized form of insulin must be synthesized" in order for ionophoresis to be possible and states the permeability of human skin to high molecular weight polymers to be "questionable". Other difficulties discussed in this paper are the association of commercial insulin rendering the impermeability to insulin of human skin as "almost certain" and the weak ionization of insulin as "mitigating against successful transcutaneous electronic (sic) transfer of the drug".

OBJECTS OF THE INVENTION

It is an object of the present invention to administer normal, unmodified protein drugs transdermally to humans and other animal patients by means of a locally applied electric field.

It is a further object of the invention to administer protein drugs transdermally in an electric field regardless of the degree of ionization or the amount of ionic charge on the protein.

It is yet another object to maximize the transdermal administration of protein drugs by eliminating or minimizing the association of protein drugs in aqueous media.

It is still another object to administer protein drugs transdermally by an electric applicator which occupies minimal area, gives the patient minimal discomfort, generates sufficient current density with minimal size and weight, and operates effectively under a wide variety of skin conditions.

It is yet a further object to administer protein drugs transdermally by electrolytic devices without irritation or reddening of the skin, and without tingling or other sensations.

Other objects of the present invention will be apparent to those skilled in the art.

SUMMARY OF THE INVENTION

The present invention utilizes a new chemical composition for transdermal transport to the blood stream of the patient by electrolytic means comprising
(a) a protein,
(b) a cosolvent with negative Setschenow constants, and
(c) water.

Protein comprise natural and synthetic modifications of different solubility: albumins, globulins, prolamines and of different functional forms: enzymes, hemoglobin, hormones, viruses, genes, antibodies, and nucleic acids, and polypeptides with more than about 20 aminoacid units.

Proteins vary in molecular weight from polypeptides of about 2000 daltons to a single strand of insulin, about 5800 daltons, to megamolecules such as tobacco mosaic virus, about 40 million daltons.

The agent for dissociating protein aggregates preferably has negative interaction parameters for both the average peptide and average methylene group (Setschenow constants), their sum, and also a negative standard free energy of transfer from water to a solution of that agent.

Water means liquid water at normal, ambient temperature, pressure, and other possible conditions (e.g. gravity) with no perturbations (e.g. no radiation, electric, magnetic, or any other possible fields).

Other useful additives may also be present, such as buffers, biocides, preservatives, or stabilizers.

The novel chemical composition of the present invention is intended for use in a transdermal electrolytic applicator comprising:

at least two electrode elements forming the applicator and separated by barrier means, reservoir means containing the chemical composition of this invention, an electronic/electrolytic circuit, including a power source, for supplying electric power to the electrodes and reservoir, cover means partially enclosing at least the reservoir means, and adhesive means for holding the applicator to the patient's skin, whereby the protein may be transported from the reservoir through the skin to the patient's bloodstream.

DESCRIPTION OF THE PREFERRED EMBODIMENTS OF THE INVENTION

Simple proteins are homo or hetero condensation polymers of aminoacids which are linked by formation of amide bonds from the amino group of one aminoacid and the carboxylic acid group of another. Conjugate proteins contain amino acid moieties plus nucleic acids, carbohydrates, lipids, or other chemical classes. Proteins may be fibrous, globular, pigmented by metals, crosslinked, or aggregative. The 20 alphaamino acids necessary for mammalian life constitute essentially all the "building blocks" of protein macromolecules.

Proteins can vary widely in molecular weight from a few thousand daltons, as in glucagon (29 peptide units), through tens of thousands of daltons, as in six-stranded insulin, to millions of daltons as in viruses. In order for large proteins to be transported through the skin, it is preferable that the protein be unassociated. If the protein is single-stranded, the cross-section of the linear macromolecular would be only a few square Angstroms even if the entire folded, convoluted, or random polymer is large in radius of gyration.

In copending application Ser. No. 012,889 filed concurrently on Feb. 10, 1987 is disclosed another invention entitled "Electrolytic Transdermal Delivery of Polypeptides", wherein is treated the case of polypeptides, mostly hormonal, with from about 3 to about 20 peptide moieties.

Insulin is a highly studied protein illustrating the importance of nonassociation. One multi-looped strand of insulin is a polypeptide with 51 aminoacid units having a molecular weight of about 5800 daltons Normal commercially available insulin, whether human, bovine, or porcine, is an association of six such multi-looped strands having a molecular weight of about 35,000 daltons. In order for insulin to be delivered transdermally in controlled meaningful amounts, it is preferable that it be totally unassociated in an electrolytic transdermal device. Until this invention, a composition and device for solving this problem had not be found. Other proteins which may be transdermally delivered to the patient are glucagon, calcitonin, protamine, adrenal cortex hormones and various globulin fractions, and the like.

In order to appreciate the importance of the present invention resulting in the nonassociation of proteins in water, it is helpful to understand the structure of proteins and of liquid water. Water is not a simple liquid, as is for example liquid argon. The HOH molecule is an isosceles triangle with a central angle of 104.52°; the H-O distance is about 1.41 Angstroms. Liquid water has a tetrahedral structure with an O-O distance of 2.76 Angstroms, an angle of 109.46°, and highly hybridized 2s and 2p orbitals. There are in fact nine different forms of ice structures, illustrating the variety of structures possible for water liquid. Since ice contracts on melting between 0° and 4° C., water has an "open" structure (cf. germanium, which also contracts on melting). Water has strong, directional forces which lead to a high dielectric constant for its nonideal structure. Ammonia and methane which have molecular weights similar to water are gases at ambient conditions not liquid, thus showing the difference between normal liquids and the strong dipole-dipole interaction in liquid water which has a high boiling point, high melting point, high enthalpy and high entropy of vaporization.

There is a strong repulsion between water molecules at an "interpenetration" distance of less than 2 Angstroms. At intermediate distance of 2-5 Angstroms there is strong hydrogen bonding between water molecules, which have a coordination number of 4. The enthalpy of sublimation of ice is 11.65 kcal/mole, much higher than simple dipole interactions, but much less than that of a chemical bond.

There have been many proposed descriptive models for the structure of liquid water, such as:

(a) in interstitial model of ice whose cavities are filled with water,
(b) quartz-like aggregates,
(c) water as a hydrate of itself,
(d) flickering clusters of cooperative H-bonds;
(e) a two-structure, mixture model.

Chemists have known for decades that water forms clathrates with xenon, chlorine, methane and other molecules and therefore must have cavities. The structure of liquid water depends on the distance and angles of H-bonds. In a two-dimensional sense, water is a hexagonal array of "aromatic" structures.

The solubility of argon in "structured" water is about one-tenth that of argon in alcohols As temperature increases from 0° to 30° C. the solubility of argon in water decreases while that in alcohols increases, thus showing a decrease in water's cavities from 0° to 30° C. The change in entropy of methane in water is about −15 to −20 e.u. but in alcohols, dioxane, and cyclohexane is about −1 e.u. The change in enthalpy of methane in water is about −3000 cal/mole, but in the same organics is 200–500 cal/mole. The process of solution may be modeled as "forming a cavity" then introducing the solute into that cavity. In a normal fluid the energy to form the cavity is positive, then filling the cavity is minus (attractive). Since water already has cavities present, there is about zero energy to form such and negative energy to dissolve the solute (fill) the cavity.

Adding some nonpolar nonelectrolytes such as ether, methyl acetate, dimethylsulfoxide structure water i.e. reinforce water structure and decrease its compressibility. Some small ions e.g. lithium and fluoride also reinforce the structure of water.

Conversely, most ions, iodine, methyl halides, small aminoacids, urea, and other polar nonelectrolytes are "structure breakers" of water.

Precise analysis of the structure of water may be a complex matter, yet it is a description of only one substance. Precise description of proteins dissociating if already dissolved, covers much broader phenomena, since there are many proteins and many cosolvents or dissociation agents to coact with water.

Just a litany of some of the terms used to name the phenomenon hints at the problems in precisely describing the interaction of protein/agent/water:

Association/disassociation, self-association, polymerization/depolymerization, gelation, intracellular aggregation, binding, multidomain folding, hydrophobic stabilization, helix promotion, random coil promotion, denaturation, lyophilizing, perturbation, demetalization, hydrophobic interactions, subunit contacts, assemblies, and molecular weight transitions.

The conformation of proteins in solution is dependent at a minimum on the concentration of protein, pH, solvent composition, ionic strength, ionic charge on the protein, solvent dielectric properties, presence of cosolutes, shear stresses, and the presence of heterogeneous third bodies such as surfaces of the container, granules, and the like.

It is generally accepted that the coniiguration of proteins in aqueous media comprises folded macromolecules with hydrophobic domains forming a central core and hydrophilic domains oriented toward the aqueous perimeter. The process of dissolution is difficult to describe in detail, but the energetics of the solution process can be determined in a straightforward manner. Much information about solution, disassociation, denaturation, coiling, gelation, unfolding, and other changes in so-called tertiary and quaternary structures may be gained from a detailed study of solution and/or gelation of proteins in water and water containing other cosolvents or "agents".

The primary structure of a protein is the term used for the sequence of aminoacids as they appear along the chain of the macromolecule. The local organization of the chain e.g. helix formation, random coil, folding is termed secondary structure. The overall spatial arrangement of the protein on the atomic level, what X-ray crystallography shows, is the tertiary level of structure. For insulin, this was published by Hodgkin et al in *Nature*, vol 224, Nov. 1, 1969 (Centenary issue) at pp. 491–495. The quaternary structure is that of several chains which may form different regions with different properties e.g. a dumbbell-like structure with a flexible middle rod and two hard ends. The function of the regions may vary. In hemoglobin, 4 myoglobins group to form a dumbbell shape with a molecular weight of about 17,000 daltons with the oxygen-bearing function associated with the two harder spheres on the ends rather than the flexible part in the middle.

The dissociation agents of the present invention greatly affect quaternary structure, are irrelevant to tertiary structure, may affect secondary structure, and have no effect on primary structure of polypeptides.

The effect of a solvent such as water on a protein can be described in terms of an equilibrium constant $K_d$ and the standard free energy of dissociation $F^o$, when a protein dissociates from e.g. hexamers to dimers or single-stranded subunits e.g. insulin in water. Often these different fragments can coexist in a series of equilibria e.g. earthworm hemoglobin can have duodecamers, hexamers, tetramers, dimers, and single fragments, at the same time at intermediate concentrations of a pure solvent or one with a dissociation agent such as propylurea or sodium perchlorate present. When such an added dissociation cosolvent is present there are two dissociation constants $K_{DW}$ and $K_{DAW}$, where DW designates pure water and DAW designates added agent and water. Also, the interaction of the added agent and the protein involves the binding constant $K_B$.

For proteins binding constant $K_B$ is the summation of two terms: a polar component $K_P$ related to the peptide bond —NHCOO— and a hydrophobic component $K_H$ related to the average hydrophobic moiety —CHR—, different for each aminoacid but averagable. The constant is related to energetics by the Nernst equation. So $$F^o_{DW} = F^o_{DAW} - mNRT (K_p + K_H)[da],$$

when m is the number of fragments and N is the number of binding sites and [da] is the concentration of the dissociation agent cosolvent.

When a solid protein is in contact with a well-stirred solvent such as water for a long time (e.g. a week) an equilibrium saturated solution is established:

$$K_{eq} = -RT \ln C_{sat}$$

When another compound is added to the water, such as an electrolyte or a nonelectyrolyte, a different $C_{sat}$ is established at equilibrium. This other value will normally be different from $C_{sat}$ for pure water. The higher the concentration of the added agent, the higher (or lower) the saturated concentration of the protein. When one graphs the log $C_{sat}$ against the molarity of the added agent, a straight line is formed. The slope of this straight line is known as the Setschenow constant for that agent. Since the equation above has a minus sign in it, those agents which aid solubility and dissociation, e.g. urea or sodium perchlorate, have a negative Setschenow constant, and those agents which decrease solubility and dissociation, e.g. sodium or ammonium sulfate have positive Setschenow constants.

$$K_x \approx -K_B/2.303$$

The Setschenow constant $K_s$ has peptide and hydrophobic components. As shown above, the Setschenow constant can be approximated by negative $K_B$ divided by log transform constant 2.303. Since negative standard free energies of transfer indicate spontaneous reactions, negative $F^o$ values for transfer from water to a mixture of water and the cosolvent indicate dissociation. The more negative, the more dissociated. Table 1 gives Setschenow constants for average peptide and hydrophobic groups, their sum, as well as free energy of transfer values for a variety of cosolvents, as taken from a paper by Herkovits et al., Journal of Colloid and Interface Science, vol. 63, No. 2, p. 232 of February 1978. The lower the position in Table I, the better the dissociation agent.

Since thermodynamics is a description of the ultimate reality, the last column listing free energies of transfer shows those agents which are preferred in practicing the present invention, those agents with negative standard free energies. The Setschenow constants are helpful, however, in appreciating

TABLE I

| Agent | Setschenow Constants For peptide | For —CH2— | Sum | −F.° tr cal/mol |
|---|---|---|---|---|
| Sodium sulfate | −0.013 | 0.085 | 0.072 | 98 |
| Potassium fluoride | −0.027 | 0.05 | 0.023 | 31 |
| Ethanol | +0.037 | −0.014 | 0.023 | 31 |
| Dioxane | +0.029 | −0.013 | 0.016 | 22 |
| Sodium chloride | −0.037 | 0.033 | −0.004 | −5 |
| Sodium acetate | — | — | −0.009 | −12 |
| Sodium bromide | −0.037 | 0.025 | −0.012 | −16 |
| Calcium chloride | −0.077 | 0.063 | −0.014 | −19 |
| Sodium proprionate | — | — | −0.017 | −23 |
| Urea | −0.018 | −0.01 | −0.028 | −38 |
| Sodium butyrate | — | — | −0.038 | −51 |
| Propylurea | — | — | −0.047 | −64 |
| Sodium thiocyanate | −0.077 | 0.007 | −0.07 | −96 |
| Potassium iodide | −0.083 | 0.01 | −0.073 | −100 |
| Sodium perchlorate | −0.097 | 0.021 | −0.076 | −104 |
| Sodium iodide | −0.087 | 0.01 | −0.077 | −105 |
| Guanidine hydrochloride | −0.061 | −0.027 | −0.088 | −120 | how the agent is useful. The "sum" column of interaction with peptide linkages in the polypeptide plus the interaction with the hydrophobic moieties is directly linked to the free energy column by the Nernst equation. It is the peptide interaction number and the hydrophobic or "methylene" number, which show how a dissociation agent works.

Urea, guanidine hydrochloride, or any other compound which has two negative parameters interact with the entire macromolecule to disaggregate the quaternary structure and perhaps unfold the secondary structure and are especially preferred for this invention. Sodium perchlorate, potassium iodide, and the like interact so strongly with peptide bonds that protein does not appreciably inhibit dissociation or unfolding of the entire protein. These agents may be useful in practicing the present invention. Ethanol, dioxane and other organics strongly react with the hydrophobic areas, usually the core of proteins, but not enough to overcome the nonpolar nature of organic solvents. Data on ethanol diverges, however Such agents have limited utility in practicing this invention Agents which have two positive components for their Setschenow constant and hence a positive standard free energy of transfer do not appear on Table I. Water-soluble amides with more than three carbon atoms are known also to be good dissociation agents but their Setschekow constants are not readily available and do not appear in Table 1 They are also encompassed in the scope of the present invention.

Electrophoresis is the transport of both solute and solvent in an electric field. Ionophoresis is the transport of charged ions by coulombic attraction/repulsion in an electric field. Electroosmosis is the transport of solvent in an electric field.

Many workers in the prior art overemphasized ionophoresis and underestimated electroosmosis in their analysis of both the best modes for and problems associated with transdermal delivery of drugs by electrolytic means. In fact, the essence of transdermal, electric-powered delivery of drugs is that control and maximization is central regardless of whether the drug is transported by coulombic attraction/repulsion or electroosmatic solvent streaming. In the present invention, unlike the prior art, Faraday's law is irrelevant. In many situations, especially in the transdermal delivery of proteins such as insulin, more drug is carried by electroosmosis than ionophoresis, so that the amount of charge or degree of ionization of the protein is not important. Before the present invention this fact was not appreciated. Prior workers attempted to improve ionophoresis by increasing charge density on the protein by oxidation or hydrolysis. For this invention the value of charge density on the drug does not control the dosage.

Electronic conduction is the movement of electrons in an electric field Electrolytic conduction is the movement of ions in an electric field Prior to the present invention, many workers failed to communicate their results well or to explain their ideas well because of confusion regarding the flow of electrons and the flow of ions. In the applicator of the present invention, current flow in the electrodes is electronic and current flow in the reservoir and through the skin is electrolytic, but it is possible to have some electronic flow along the chain of a protein in an electric field in water or aqueous media.

The values of the electrical variables in the practice of the current invention in vivo are those pertaining to electroosmosis not ionophoresis. The current density may be from about 0.5 ua/cm$^2$ to about 1 ma/cm$^2$, preferably about 0.5 microampere/cm$^2$ to about 10 microampere/cm$^2$ rather than the 1 milliamperes/cm$^2$ to 5 milliamperes/cm$^2$ values associated with ionophoresis. The voltage impressed for operating the applicator of the present invention ranges from about 1 to about 40 volts rather than the 50 to 100 or more volts advisable for ionophoresis. Likewise the migratory flow of water in an electrolytic field are the much higher values of about 0.001 ml/cm$^2$/hr to about 0.005 ml/cm$^2$/hr constant of electroosmosis not the typical adventitious values for ionophoresis, following Faraday's law which impels only ions.

It is highly preferred that the current density employed in the present invention be low enough to prevent any irritation, reddening, inflammation, or erythema in the skin of the patient.

The chemical composition of the present invention comprises three components: protein drug, cosolvent with negative Setschenow constant, and water. One can also consider the "cosolvent" as a cosolute. In addition, the composition may contain salts for physiological balance, buffering agents, disinfectants, antibiotics, preservatives, or other additives.

It is sometimes useful to add chelating agents to the chemical composition of this invention in order to demetallize a protein. Demetallization changes the quarternary structure of protein by removing metallic cations, which bind together polypeptide chains. Some of the metal ions which are integral parts of protein structure are magnesium, zinc, copper, chromium, cobalt, nickel, iron, and manganese. Many conventional chelating agents may be employed such as the salts of ethylenediaminetetraacetic acid (EDTA). Other conventional chelating agents may also be used.

Figure 1:
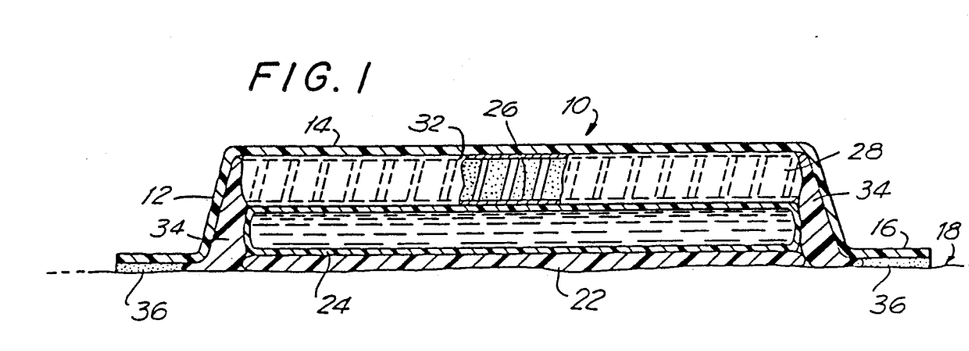
FIG. 1 is a cross-sectional view of one type of electronic/electrolytic drug applicator employing the chemical composition of the present invention to administer proteins to a patient transdermally.

FIG. 1 shows generally drug applicator 10 comprising outer cover 12 having a raised portion 14 and an outer-edge lip 16 in contact with the skin 18 of the patient. The layered structure of the drug applicator 10 can be any convenient and effective size or shape such as rectangle, oval, circle, or splayed shape to fit crevices at interfaces of body parts. The size of the applicator may range from about 10 cm$^2$ to about 200 cm$^2$ depending on its use and the species, age, and size of the patient.

Applicator 10 often has generally a structure of horizontal layers. The layer shown in FIG. 1 as that closest to the skin 18 is an optional semipermeable membrane 22 through which the drug diffuses for deposition on skin 18. Optional membrane 22 may be constructed of semipermeable, cellulose acetate, poly(vinyl chloride), or regenerated cellulose.

Above optional semipermeable membrane 22 is a reservoir, region, or pouch 24 for holding the supply of the protein to be electrolytically delivered and a reservoir for the other electrode. Preferably reservoir 24 defines a closed space and is flexible. Typical materials used in forming pouch 24 are rayon floc, polyurethane sponge, and hydrophilic adhesive in latex form. This reservoir may also consist of a hydrophilic gel. For containing the protein solution or suspension of the present invention, reservoir 24 may range from about 0.01 ml to about 15 ml in volume, preferably about 0.15 ml to about 0.9 ml for about a week's continual administration of a protein drug in amounts ranging from about 500 nanograms to 1 mg per day, depending on the size, species, and age of the patient. The gel, pouch, or walls of the reservoir 24 must be microporous enough for transfer of the solvent, solution, or suspension of the protein by the electric field, but not so porous to allow leakage of the suspension or solution of the protein drug. The choice of whether or not to employ optional semipermeable membrane 22 is interrelated with the choice of design and material of reservoir 24, because their functions may overlap.

The next higher layer above reservoir 24 as shown in FIG. 1 comprises extended contact 26 which is preferably the lower face of battery 28. Contact 26 preferably is flexible enough to conform to the surface of the skin and also is electronically conductive. Preferred materials for contact 26 are electric-conducting polymers, carbonized plastic films, or plastic surfaces loaded with or painted with highly conductive powdered or solid carbon or graphite.

Battery 28 comprising the next layer may be made up of a group of cells internally connected in series to obtain the desired voltage necessary to obtain the electrophoretic action with the particular protein Orientation of battery 28 depends on the direction of endosmotic flow which is usually from the anode. With regard to battery 28, it should be noted that any conventional miniaturized battery cells now generally available can be employed, arranged and connected in series to obtain the desired operating voltage. In addition, the technology now exists for batteries made of thin, flexible sheets of an electrically conductive polymer with high surface area relative to its thickness to provide adequate current densities. One such so-called plastic battery is described in "Batteries Today", Autumn 1981, pages 10, 11, and 24. When such a battery is employed, sheets may be layered to place the cells in series, and an effective compromise between number of sheets and surface areas of sheets is achieved by layering them diagonally, as shown somewhat schematically in FIG. 1. Of course, battery selection also depends on such factors as the degree of conformability desired, voltage and current densities required for a specific application, and time of discharge.

In FIG. 1, above battery 28 is electrical contact 32, which preferably is similar in design and material to electrical contact 26 and forms the opposite side of the battery.

Cover 12 encloses all the previously listed layers of drug applicator 10 and is made of flexible, conductive material such as a plastic polymer impregnated with carbon, electrically conductive itself, or carbonized on its surface. Insulating material 34 fills the space between the side walls of raised portion 14 and the various aqueous layers containing electrolyte. Suitable insulating materials are polyester, silicones, and any other drug-compatible plastics. Alternatively, a totally insulating cover may envelope all of the working components previously named.

In order for drug applicator 10 to make good contact with and stick to the patient's skin 18 electrically-conductive adhesive 36 is applied under the edge of lip 16. Suitable conducting adhesive materials are those filled with powdered conductors such as carbon or graphite.

It will be seen that the arrangement described above forms a complete electric circuit from one side of battery 28, cover 12, adhesive material 36, skin 18, microporous membrane 22, liquid reservoir 24, and back to battery 28. Also the reservoir may be divided into separate anode and cathode compartments with an insulator between and the battery in a separate compartment.

The electrical operation of the drug applicator may be carried out in many modes, including that of uniform direct current. The impressed voltage from the power source may be pulsed with a wide variety of pulse width and frequency. A sawtooth voltage or other types of reversing, sinusoidal, or alternating voltage sources are also within the disclosure of this invention.

The types of batteries and their orientation are disclosed inter alia in U.S. Pat. Nos. 4,557,723 and 4,640,689. The types of circuits which may be employed are also disclosed in various of the above-cited related applications.

The preferred proteins to be administered by the composition of the present invention are compounds, such as insulin, protamine, glucagon, calcitonin, proteinaceous adrenal hormones, and the like. Other proteins such as albumin may be administered transdermally by an electrolytic device. Proteins related to blood fractions such as globulins, tetanus, rabies and other proteins or antibodies may also be employed, as may be enzymes or other proteinaceous entities.

Quite arbitrarily this disclosure terms any polypeptides with more than about 20 alphaaminoacids as a "protein". Thus glucagon (29 units), calcitonin (32 units), and corticortropin (39 units) are here termed "protein", as is disassociated insulin (51 units). Polypeptides from about 3 to about 20 alphaamino acid units are termed "polypeptides" and are not preferred in the practice of the present invention.

Having described the inventive composition of protein dissociating agent with negative Setschenow constants, and aqueous electrolyte and having described an embodiment of the electrolytic drug applicator for transdermal delivery of proteins, we now illustrate the invention in the following Examples. These Examples, however, are intended only to illustrate not limit the scope of the instant invention, which may be carried out by other means and still be covered by the teachings of this disclosure.

EXAMPLE 1

This Example illustrates the preparation of small electrolytic transdermal devices with side-by-side reservoirs and electrodes. Another possible design is that of a "matted-photograph" with the drug reservoir anode surrounded by an insulated frame-shaped cathode, as shown in FIG. 1.

The side-by-side reservoirs and electrodes have a rayon gauze next to the skin (Johnson & Johnson Co., New Brunswick, N.J.). Two matted rayon pads 5 cm×8 cm×0.5 cm are topped by U-shaped polyester film 0.1 mm thick coated with 0.02 mm layer of conducting graphite Paint (Bertek Corp., St. Albans, Vt.) surrounding a central insulator of 0.2 mm Mylar polyester film (duPont Co., Wilmington, Del.). The top surface of the U-shaped graphitized polyester film is connected to a 9V battery (El Power Corp., Santa Anna, Calif.). The periphery of the felted reservoir pads and electrodes plus an insulating band in the gauze base between them is RTV silicone resin (Dow Corning Co., Midland, Mich.). Surrounding the top and sides of the device is surgical adhesive tape (Hy-Tape Surgical Hosiery Corp., New York, N.Y.). Each of the reservoirs can hold 6 ml of aqueous fluid.

EXAMPLE 2

This Example (8670Z) illustrates the transdermal delivery of insulin by the composition of the present invention to rabbits employing urea.

Eight healthy albino rabbits were equilibrated for 24 days under standard clinical conditions. Their backs were clipped the day before, washed with castille soap on the day of the test anJ a 7.5 cm×10 cm electrolytic patch containing two 6 ml reservoirs applied, as prepared in Example 1. The negative reservoir contained 6 ml with 500 IU of regular human insulin (Lilly, Humilin R) and 1% (0.16 M) urea. The positive reservoir contained 5 ml of 0.9% saline The patches were held next to the clipped skin with elastic tape, and the rabbits restrained for the 10 hours of the test.

The blood was collected from the medial artery of each rabbit's ear at 0,4,5,6,7,8,9, and 10 hours of the test. Blood glucose was determined with an Accu-Check 11 blood glucose monitor (Boehringer Manheim Co., Ridgefield, Conn.). Radioimmuno assays (RIA) were performed with a Pharmacia Corp. (Piscataway, N.J.) Insulin 100 RIA kit.

Radioactivity values were standardized and counted on a Tracor Corp (Austin, Tex.) gamma counter.

Patch Model Y provided twice the current density as patch model X.

The insulin data for all eight rabbits are shown in Table 2A for this Example. One rabbit with patch Y model died at the eight-hour point from insulin overdose. Inspection of Table 2A shows that transdermal delivery was effective in five of the eight rabbits and marginal in one for this period of time.

Figure 2:
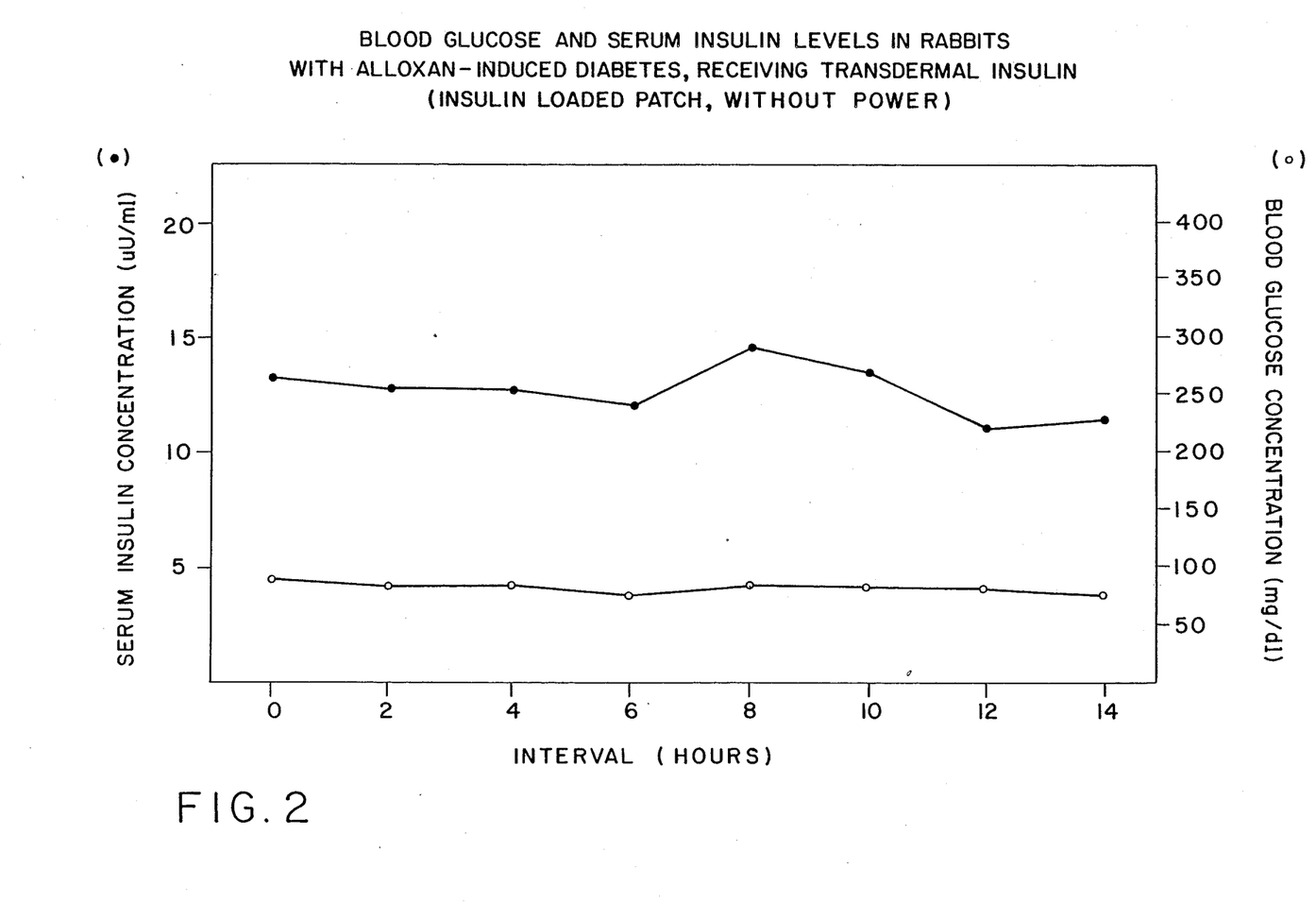
FIGS. 2 and 3 are graphs of diabetic rabbits which received transdermal insulin from insulin loaded patches with and without power.
Figure 3:
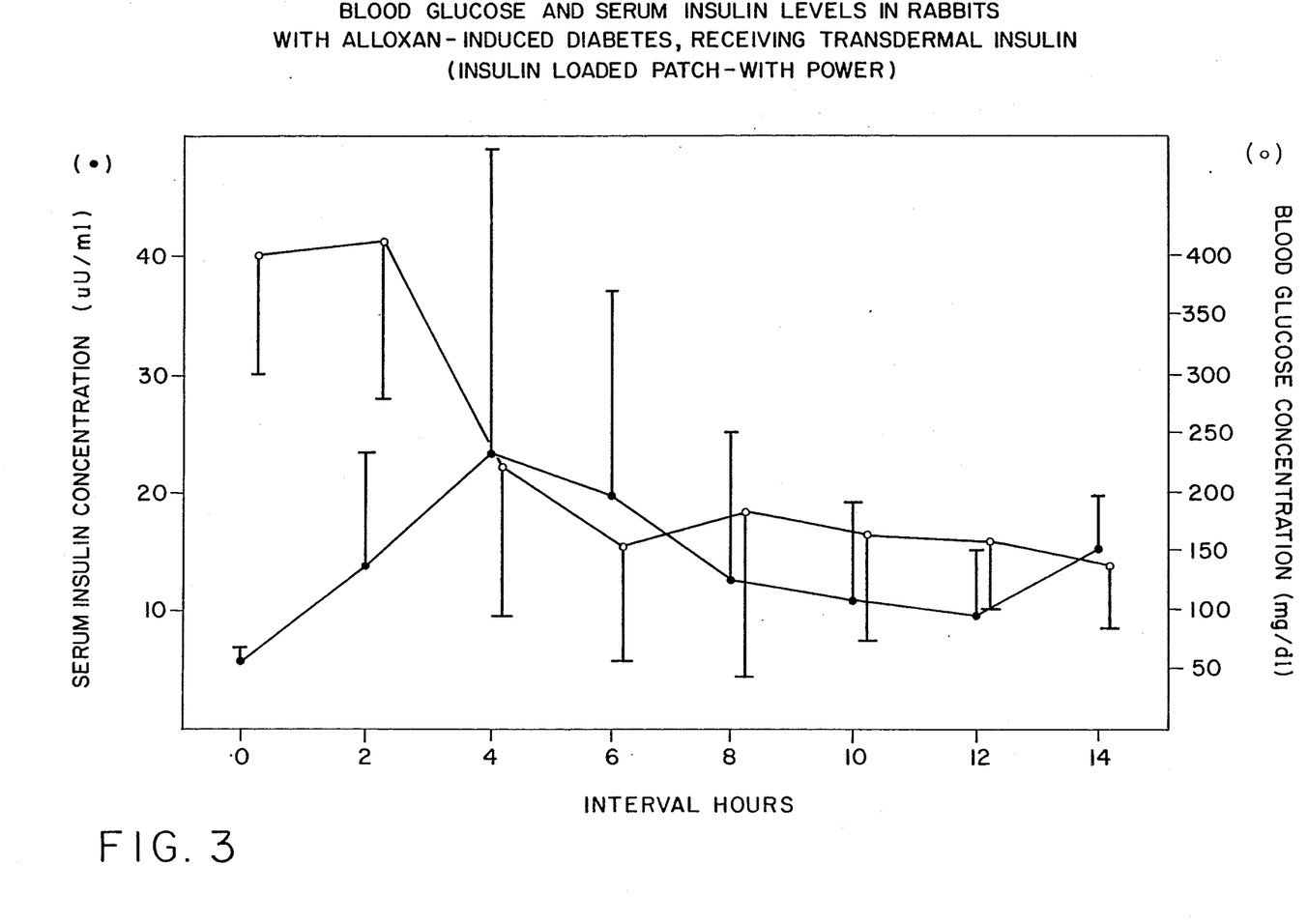

Table 2B shows blood glucose values for all eight rabbits at the various test points. Inspection of Table 2B shows that glucose levels were lowered in varying degree in seven of the eight rabbits. See the graphs FIGS. 2 and 3 for diabetic rabbits.

TABLE 2A

SUMMARY OF INSULIN CONCENTRATION IN SERUM FOLLOWING TRANSDERMAL DELIVERY OF INSULIN CONTAINING 1 MG UREA PER ML

| Rabbit No. | Patch Model | Insulin Concentration in Serum (uU/ml) Interval (Hours) | | | | | | |
|---|---|---|---|---|---|---|---|---|
| | | 0 | 4 | 5 | 6 | 7 | 8 | 9 | 10 |
| 1281 | X | 6.9 | 57.1 | 58.1 | 35.4 | 37.3 | 30.0 | 21.0 | 29.3 |
| 1282 | X | 3.3 | 4.2 | 3.7 | 4.2 | 4.0 | 4.0 | 3.7 | 4.2 |
| 1284 | X | 4.4 | 4.4 | 4.1 | 4.4 | 4.0 | 3.8 | 3.8 | 4.2 |
| 1285 | X | 3.7 | 12.3 | 11.6 | 12.8 | 11.6 | 8.8 | 11.2 | 12.6 |
| 1286 | Y | 3.8 | 3.9 | 3.9 | 3.5 | 3.9 | 3.8 | 3.7 | 5.5 |
| 1287 | Y | 3.6 | 4.5 | 7.6 | 5.8 | 8.5 | 9.3 | 24.0 | 175 |
| 1288 | Y | 3.5 | 9.9 | 13.7 | 10.4 | 13.4 | 11.4 | 11.7 | 28.7 |
| 1289 | Y | 6.9 | 187.0 | 197 | 217 | 211 | 198$^a$ | | |

$^a$Animal died at 8 hours.

TABLE 2B

SUMMARY OF BLOOD GLUCOSE LEVELS FOLLOWING TRANSDERMAL DELIVERY OF INSULIN CONTAINING 1 MG UREA PER ML

| Rabbit No. | Patch Model | Blood Glucose Concentration (mg/dl) Interval (Hours) | | | | | | |
|---|---|---|---|---|---|---|---|---|
| | | 0 | 4 | 5 | 6 | 7 | 8 | 9 | 10 |
| 1281 | X | 131 | 79 | 65 | 64 | 58 | 47 | 39 | 32 |
| 1282 | X | 133 | 100 | 131 | 110 | 120 | 114 | 113 | 97 |
| 1284 | X | 134 | 124 | 132 | 121 | 112 | 113 | 120 | 117 |
| 1285 | X | 107 | 103 | 101 | 92 | 94 | 87 | 82 | 80 |
| 1286 | Y | 115 | 121 | 135 | 128 | 137 | 127 | 129 | 122 |
| 1287 | Y | 135 | 136 | 140 | 121 | 101 | 88 | 82 | 82 |
| 1288 | Y | 138 | 115 | 104 | 94 | 90 | 75 | 79 | 67 |
| 1289 | Y | 119 | 38 39$^a$ | 22 | 29 | 57 | 35$^b$ | — | — |

$^a$Sample repeated to confirm original assay.
$^b$Animal died at 8 hour interval.

COMPARATIVE EXAMPLE 1

This Comparative Example illustrates the necessity of having a compound with negative Setschenow constants in the composition of the drug reservoir in order to achieve appreciable delivery of a protein such as insulin to the bloodstream of the patient. Without a dissociating agent only very small amounts of insulin are delivered by electroosmosis.

Employing patches prepared by the procedure of Example 1 and insulin tests as in Example 2, four albino rabbits were treated with a patch whose anode reservoir held 5 ml containing 500 IU of Humilin R (Lilly Co., Indianapolis, Ind.) but no dissociating agent and whose cathode compartment contained 0.9% saline.

Table CE shows the insulin values in the rabbit blood samples at the hour points indicated. Because the insulin transport was so low without the dissociating agent of the present invention, blood glucose data were not obtained.

Disregarding the two aberrant values, inspection of Table CE shows that only two rabbits (Nos. 367 and 547) received a measurable dosage of insulin.

TABLE CE

| Rabbit No. | Insulin Values (uU/ml) at Intervals (Hours) | | | | | | |
|---|---|---|---|---|---|---|---|
| | 0 | 1 | 2 | 3 | 4 | 5 | 6 |
| 364 | h | 5.9 | 3.6 | 3.6 | 4.1 | 4.7 | 4.6 |
| 365 | 4.1 | 4.7 | 3.9 | h | — | 3.4 | 10.8 h |
| 367 | 13.5 h | 10.0 | 11.3 | 28.1 | 33.3 h | 25.4 | (104)sic |

TABLE CE-continued

| Rabbit No. | Insulin Values (uU/ml) at Intervals (Hours) | | | | | | |
|---|---|---|---|---|---|---|---|
| | 0 | 1 | 2 | 3 | 4 | 5 | 6 |
| 385 | 14.6 h | 3.4 | 5.3 | 7.4 | 6.3 | 4.9 | (231)sic |
| 545 | 10.7 | 8.0 | 5.1 | 7.7 | 8.3 | 6.9 | 14.2 |
| 547 | 5.4 | 5.2 | 9.9 | 9.9 | 12.8 | 18.6 h | 17.5 |
| 549 | 12.3 | 10.5 | 7.4 | 7.0 | 8.2 | 10.8 | 12.0 |
| 551 | 3.0 | 3.7 h | 3.2 | 10.1 | 4.2 | 4.7 | 5.4 | h shows samples with marked hemolysis

MODEL EXAMPLES

Model Example 1

This Example illustrates the use of a protein composition of the present invention in an electrolytic transdermal applicator to obviate the use of a series of injections and to introduce a protein drug to the bloodstream of the patient gradually without the trauma of one or more bolus injections.

Twelve electrolytic patches as in Example 1 employing a positive drug reservoir of 6 ml contain 2 mg activity protamine sulfate (Lilly, Injection USP) per ml, 1.5% sodium iodide, and the 0.9% sodium chloride found in commercial USP protamine. The negative reservoir contains 0.9% saline.

The standard blood clotting time of each of 12 albino rabbits, prepared as in Example 2 is determined. At zero time the 12 rabbits are fitted with the electrolytic transdermal patches employed in Example 2. The six control patches have no batteries. At the three-hour point all 12 rabbits are injected intravenously with 500 units of Heparin Sodium Injection USP (Upjohn Co., Kalamazoo, Mich.). At the three-hour 20-minute point the coagulation time of a 1 ml sample of blood taken from all 12 rabbits is measured.

It is found that the rabbits fitted with the operating protamine protein electrolytic transdermal patch of this invention have a clotting time considerably shorter than those control rabbits with the protamine sulfate transdermal patch inoperative. One notes that rapid injection of protamine may cause dyspnea, flushing, bradycardia, and hypotension in humans.

Model Example 2

This Example illustrates the use of a larger-sized electrolytic patch for administering calcitonin, a 32-unit polypeptide to human adults to lower the calcium level in their blood and inhibit bone resorption (Paget's disease). As a beneficial side effect slow delivery of calcitonin improves impaired auditory nerves, lowers high cardiac output, and treats postmenopausal osteoporosis.

In the same manner as in Example 1, electrolytic patches are prepared based on 12 cm by 8 cm by 0.6 cm felted rayon pads. Three 3-volt, nickel-cadmium, wafer batteries are used in series on the top. The entire side periphery and cover is made from 0.15 mm PVC film No semipermeable ultrafiltration membrane is employed between the bottom of the two side-by-side reservoirs and the skin.

The drug reservoir compartment comprises 12 ml Calcimar synthetic salmon-calcitonin (USV, Tarrytown, New York) containing per ml 200 IU calcitonin-salmon, 5 mg. phenol biocide, and trace amounts of sodium chloride, sodium acetate, acetic acid, and sodium hydroxide for buffering and tonicity all in 0.2 M sodium perchlorate, which has a negative Setschenow constant The current( density is 5 ua/cm$^2$, which delivers 50 IU per hour Monitoring four adult male subjects over a 2U-day period shows a lowering of calcium in the subjects averaging 12%, a distinct advantage over repeated injections which lowers blood calcium level only 9% in general.

Model Example 3

This Example illustrates the use of the composition of the present invention to deliver glucagon electrolytically and transdermally in patients without the necessity of repeated injections in order to control hyperglycemia and avoid insulinoma and/or pheochromocytoma with decreased probability of the release of catcehol amines. Glucagon is a protein with 29 peptide units and comprises aminoacids 33 through 61 of glicentin. In vivo glucagon is synthesized multistranded with a molecular weight about 18,000. The commercial extract from beef and pork pancreas is single-stranded with a molecular weight of 3483.

As in Model Example 1, six rabbi s are prepared and fitted with the electrolytic transdermal patches, as in Example 2. The "return" reservoir contains 0.9% saline solution. The drug reservoir contains 100 units of Lilly Co. No. 668 Glucagon for Injection USP in 0.2 m propylurea, which has a negative Setschenow constant A current density of 3 ua/cm$^2$ is low enough to allow a controlled rise in blood sugar values Comparison of zero time blood sugar values with 8-, 16-, 24- etc. hour values for four days shows an increase in blood sugar value averaging about 12%.

Model Example 4

This Model Example illustrates the delivery of corticotropin at continuous low levels transdermally by the composition of the present invention. Human, ovine, porcine, and bovine adrenocorticotropic hormone (ACTH) are all 39-unit polypeptides differing slightly in composition at aminoacids in the 25, 31, and 33 positions.

By the same procedures employed in Model Example 3 ACTHAR-40 (Armour Co., Tarrytown, N.Y.) is introduced to eight rabbits whose levels of cortisol, corticosterone, and aldosterone in the blood are monitored every six hours for eight days. A current density of 5 ua/cm introduces the drug transdermaly at the rate of 1.5 USP units/hour. The drug reservoir contains 400 units in 0.25M potassium iodide, which has a negative Setschenow constant.

Comparison of the cortisol, corticosterone, and aldosterone levels in these rabbits shows an average increase of about 15%, when the ACTHAR is being administered, compared to the values before this eight-day test of the electrolytic transdermal device.

Many other embodiments of this invention will be apparent to those skilled in the art, but such will be within the scope of Letters Patent based on the following claims.

We claim:
1. A transdermal patch for delivering at least one protein drug to the bloodstream of the patient comprising:
    a. at least one protein drug comprising at least one nonionic protein having more than 20 peptide units, water, and a water-destructuring agent with a negative Setschenow constant, contained in a drug reservoir, and b. electrolytic means comprising a power source connected to at least one electrode in electrolytic contact with said reservoir for transdermal transport of the nonionic protein having a current density from about 0.5 microampere/cm$^2$ to about 10 milliampere/cm$^2$, impressed voltage between 1 and 40 volts, and a migratory water volume between 0.00I/ml/cm$^2$ hr and 0.0I ml/cm$^2$/hr, whereby the skin of the patient is neither irritated nor erythematized.

2. A transdermal patch as in claim 1, wherein the at least one nonionic protein drug is an insulin.

3. A transdermal patch as in claim 1, wherein the current density is between 0.5 microampere/cm$^2$, the voltage is between 3 and 10 volts, and the migrating water volume is between 0.002 and 0.005 ml/cm$^2$/hr.

4. A transdermal patch as in claim 1, wherein the water destructuring agent is selected from the group consisting of urea, alkylderivatives of urea, gaunidine salt, butanol, 2-butanol, water-soluble amides with more than three carbon atoms, sodium chloride, sodium acetate, sodium bromide, calcium chloride, sodium propionate, sodium butyrate, sodium thiocyanate, potassium iodide, sodium perchlorate, sodium iodide, any water-soluble salt with a negative Setschenow constant, and mixtures thereof.

5. A transdermal patch as in claim 1, wherein the nonionic protein or the uncharged protein at its isoelectric point is selected from the group consisting of glucagon, protamines, adrenal cortex proteinaceous hormones, calcitonin, albumins, globulins, insulins, and mixtures 6. A transdermal patch as in claim 1, wherein the nonionic protein or the uncharged protein at its isoelectric point is a polypeptide having more than about 20 peptide units.

7. A transdermal patch as in claim 1, wherein the reservoir has a liquid volume of from about 0.01 ml to about 15 ml.

8. A transdermal patch as in claim I, further comprising a semipermeable membrane on the side of the reservoir adapted to be placed on the skin of the patient.

* * * * *

UNITED STATES PATENT AND TRADEMARK OFFICE
CERTIFICATE OF CORRECTION

PATENT NO. : 4,940,456
DATED : July 10, 1990
INVENTOR(S) : Dan Sibalis and Sanford Rosen It is certified that error appears in the above-identified patent and that said Letters Patent is hereby corrected as shown below:

Col. 15, claim 3, line 2, after "$cm^2$", but before the comma, insert -- and 100 microamperes/$cm^2$ --.

Signed and Sealed this

First Day of March, 1994

Attest:

BRUCE LEHMAN

Attesting Officer     Commissioner of Patents and Trademarks